United States Patent [19]

Kljuev et al.

[11] Patent Number: 4,930,026

[45] Date of Patent: May 29, 1990

[54] FLAW DETECTOR FOR MAGNETOGRAPHIC QUALITY INSPECTION

[76] Inventors: Vladimir V. Kljuev, 3 Frunzenskava ulitsa, I4, kv. 5., Moscow; Valery S. Kozlov, Leninsky prospekt, I6, kv. 76., Minsk; Dmitry B. Volodchenko, ulitsa Novovilenskaya, 3, kv. 32., Minsk; Alexandr V. Stepanenko, ulitsa Surganova, 40, kv. 25., Minsk; Vladimir I. Baranovsky, ulitsa Minskaya, I05, kv. 4.; Mikhail I. Korolkov, ulitsa Ryabinovaya, 27., both of Bobruisk; Orest S. Semenov, ulitsa Verkhnyaya Pervomaiskaya, 53/35, korpus 3, kv. 27., Moscow, all of U.S.S.R.

[21] Appl. No.: 170,851

[22] Filed: Mar. 21, 1988

Related U.S. Application Data

[62] Division of Ser. No. 919,879, Oct. 16, 1986.

[51] Int. Cl.$^5$ .................... G11B 5/02; G01N 27/82
[52] U.S. Cl. ........................... 360/67; 324/237
[58] Field of Search ................ 324/213–216, 324/226–228, 237, 238, 239; 360/15, 67; 369/84, 85; 358/301; 346/33 F, 33 M

[56] References Cited

U.S. PATENT DOCUMENTS

| | | | |
|---|---|---|---|
| 2,740,090 | 3/1956 | Dionne | 360/15 |
| 3,484,682 | 12/1969 | Wood | 324/227 |
| 3,825,821 | 7/1974 | Forster | 324/216 |
| 4,121,288 | 10/1978 | Hickam | 324/213 |
| 4,625,167 | 11/1986 | Fitzpatrick | 324/213 |
| 4,638,378 | 1/1987 | Zanessi | 360/15 |
| 4,755,752 | 7/1988 | Fitzpatrick | 324/213 |
| 4,827,357 | 5/1989 | Kawakami | 360/15 |

Primary Examiner—Vincent P. Canney
Attorney, Agent, or Firm—Lilling & Greenspan

[57] ABSTRACT

A flaw detector includes a readout unit; a sensor of cycles or lines, and a mechanism for driving the magnitogram and a magnetosensitive transducer. A permanent memory is made as a magnetic medium and a recording magnetic head, a test data processing unit, an interface, and a computing device are provided.

7 Claims, 5 Drawing Sheets

FLAW DETECTOR FOR MAGNETOGRAPHIC QUALITY INSPECTION

This is a division of: divisional of copending application Ser. No. 919,879 filed on October 16, 1986.

BACKGROUND OF THE INVENTION

1. Field of the Invention

The invention relates to test instruments and, in particular, to methods and devices for magnetographic quality inspection of materials.

This invention can be used in civil engineering and petroleum industry for quality testing of pipes for critical applications, in mechanical engineering for detection of flaws in rolled products, welds of cylinder blocks of heavy-duty diesel engines and for measuring the size of cracks, in ship-building industry for quality testing of welds of ship hulls and reservoirs, including underwater tanks, and in other fields where products are to be tested for continuity defects in not easily accessible locations and when access is possible only from one side.

2. Description of the Prior Art

Known in the art are various methods and devices for magnetographic inspection of materials, wherein the zone to be tested is brought into contact with a magnetic medium and magnetized. The result is that magnetic leakage fluxes penetrate through the surface of the material in places where flaws occur, and are recorded on the magnetic medium. In this manner a magnetogram or "magnetic picture" of the tested material is obtained.

The magnetogram is read out in a line-by-line cyclic manner by a magnetic pickup which produces signals carrying information on the location, size, and type of flaws. In general, electrical signals supplied by the magnetic pickup can be converted into signals indicative of the quality of the material being tested. To this end, electrical signals are displayed on the monitor screen or converted into pulses controlling light indicators and devices marking flaws by paint on the tested material.

But, when the quality of critical products is to be tested, the test has to be substantiated by a document representing the quality of the tested material. This may be roentgenogram or an X-ray photograph of the tested material. It is not easy to obtain a magnetic photograph of the tested material in the course of the non-destructive inspection process by prior art techniques and devices.

Besides, the production engineer dealing with optimization of manufacturing methods, e.g. welding conditions, has to monitor the internal state of the material being treated. For this purpose, the relief of the magnetic field read by the magnetic pickup is to be presented as a color shadow picture indicative of the quality of the tested material.

In this respect, particularly interesting are attempts to develop a device for magnetographic quality inspection of materials, which includes an indication means made as a system converting the magnetogram into a color shadow picture indicative of the quality of the tested material and a printer providing a paper document of the test results. In this case, quantitative assessment of the defects in the tested material can be made on the basis of the indication signals obtained by electronic processing of information read by the magnetic pickup from the magnetogram.

Known in the art is a method of magnetographic quality testing of materials (cf., for example, U.S. Pat. No. 3,341,771, Cl. 324–37), wherein the material to be tested is magnetized, when a magnetic medium is located on the surface of said material. The magnetic medium is then removed, after it has recorded the magnetogram by the action of the magnetizing field, and said magnetic medium is placed in a device for registering the magnetogram. The device amplifies the information contained in the magnetogram and converts this information into electrical signals indicative of the flaws of the material. The device realizing this method features a magnetic pickup adapted for reciprocating motion above the magnetogram, an amplifier, and an indicator. The indicator represents the pulse signal whose shape is indicative of the quality of the material being tested.

But this method and device for magnetographic flaw detection are deficient in that workpieces for critical applications, which have complex shapes, cannot be tested for quality because the magnetogram obtained by this method cannot be directly converted into a ferrogram which is a visual representation of the magnetic relief, that can be printed on paper. Visual examination of the relief of the magnetic recording is necessary in order to detect flaws in complex workpieces, particularly in welds with reinforcement beads. The prior art method and device provide no means for processing the electrical signal, e.g. signal conversion into a color shadow picture, which is important for weld testing since the information content and resolution can be greatly improved.

Also known in the art is a method of magnetographic quality testing of rolled products, e.g. steel billets (cf., advertising booklet "Magnetographie 9.143", published in Federal Germany, 9/81 K, No. 1-81522-1672). The device realizing this method of magnetographic quality testing comprises an electronic indication unit for processing electrical signals read from the magnetogram. Test results can be registered on a paper tape by a print-out device.

This method and device can be used to determine the size and depth of the detected flaw.

However, this device has a limited application field since it can only be used for workpieces with a flat and sufficiently smooth surface. Quality testing of complex objects, e.g. welded joints, cannot be done by this device because it has no means to tune away from noises caused by the irregular surface of the material being tested, e.g. the reinforcement bead of a weld. Besides, this device has no monitor on which the color and shadow picture can be obtained to indicate the quality of the tested material. The color and shadow picture of the internal state of the material is indispensable for quality inspection of workpieces having complex shapes.

Known in the art is a magnetographic flow detector (cf., USSR Inventor's Certificate No. 482,669, Cl. GOIN 27/89, published in "Biulleten Izobreteny" No. 32, 1975), comprising a readout unit composed of a cylinder adapted to rotate about its axis, a magnetic pickup being located on the cylindrical surface thereof, and a mechanism for driving the magnetogram and the cylinder. The indicator of this device is a monitor featuring a scale and time transformation system, which is coupled to the magnetic pickup. This device can be used to provide a color and shadow picture indicative of the quality of the material being inspected. But this device can only supply single frames, which makes it difficult to automate the testing process. In addition, this device has no printout facilities and cannot, therefore, produce a paper document substantiating the results of the quality tests.

SUMMARY OF THE INVENTION

The primary object of this invention is to provide a method of magnetographic quality inspection of a material, which supplies highly reliable information on the quality of the material of complex-shaped workpieces.

Another object of the invention is to provide a method of magnetographic quality inspection of a material, when access to the workpiece is only possible from one side.

Yet another object of the present invention is to provide a method of magnetographic quality inspection of a material, whereby the information obtained can be easily and quickly reproduced in many copies.

Still another object of this invention is to provide a method of magnetographic quality inspection, whereby quantitative assessment of the quality of the tested material can be made, and location and length of any portion of the tested material can be determined.

One of the primary objects of the present invention is to provide a flaw detector realizing the method of magnetographic quality inspection of a material, whereby inspection is made more reliable and the quality of test documents is improved.

Another object of the present invention is to provide a flaw detector which offers much simpler technical means for documenting information on the test and makes this documenting process more efficient.

One more object of this invention is to provide a flaw detector whereby the information content of tests can be expanded.

A further object of this invention is to provide a flaw detector having broader potential applications.

Another primary object of this invention is to provide a flaw detector whereby the reliability and information content of tests are improved through mathematical processing of information on the quality of the material.

Another object of the present invention is to provide a flaw detector capable of quantitative assessment of the quality of the tested material.

One more object of this invention is to provide a flaw detector which is much more reliable in operation.

There is provided a method of magnetographic quality inspection of a material, which consists in that a zone of the material to be inspected is brought into contact with a magnetic medium and magnetized, a magnetogram of the material being inspected is obtained on the magnetic medium, this magnetogram is read by a magnetic pickup and amplified to obtain a signal indicative of the quality of the tested material, said information of the magnetogram being simultaneously converted into an indication signal and entered into a read-only memory unit.

Information on the quality of the material can thus be made more reliable when visually examined and in the process of documenting.

Advisably, the information entered into the permanent memory should be transformed into a ferrogram which can be later documented and copied.

In this manner, a document representing the quality of the tested material can be quickly obtained and used for high resolution interpretation.

Possibly, in order to make quantitative assessment of the quality of the material, information picked up from the magnetogram can be accumulated during one operational cycle of the magnetic pickup, and this total can be used to determine the quality of the tested zone of the material.

Advisably, the total obtained during an operational cycle of the magnetic pickup should be compared with other totals obtained in other operational cycles, the difference of these totals being used as an indication signal.

In this manner, direct quantitative assessment of the quality of the tested material can be obtained.

There is also provided a flaw detector realizing the method of magnetographic quality inspection, which comprises a readout unit made up a drum adapted to rotate about the axis thereof, a magnetic transducer located on the cylindrical surface of the drum and an information pickup unit which are coupled in series, a readout cycle sensor and a mechanism for driving the magnetogram and the drum with the magnetosensitive transducer, and a test data processing unit including an amplifier whose input is connected to the information pickup unit and which is connected in series with a monitor, and, according to the invention, is provided with a permanent memory which is a magnetic medium and a recording magnetic head connected to the amplifier.

This permits more reliable material testing by increasing the contrast of information examined visually and improving the quality of documenting the test data.

Possibly, the recording magnetic head of the permanent memory should be arranged on the cylindrical surface of the drum with a circumferential displacement in relation to the magnetosensitivie transducer which is a reproducing magnetic head, and the mechanism for driving the magnetogram should be provided with a device to carry the magnetic medium of the permanent memory.

This permits the use of simple technical means for documenting the test data, making the documenting process more readily adaptable to the manufacturing methods.

Advantageously, the magnetosensitive transducer of the flaw detector should comprise several reproducing magnetic heads disposed on the cylindrical surface of the drum so that the heads are displaced in relation to the shaft of the drum and spaced apart to a distance equal to the readout line length, and the test data processing unit should additionally comprise a switch inserted between the display device and the amplifier and connected to the output of the readout cycle sensor.

In this manner the information content of the quality testing is expanded.

Advisably, the test data processing unit of the flaw detector should comprise a line video signal generator inserted between the display device and the switch.

This makes the flaw detector more universal by broadening its field of application.

Advisably, the flaw detector should comprise two series connected components: an interface coupled to the test data processing unit and a computing device.

This makes quality testing more reliable and expands the information content thereof by providing mathematical processing of information on the quality of the material being inspected.

The test data processing unit can comprise, connected in series, an analog-digital converter whose inputs are connected to the amplifier and the display device, and a buffer storage whose output is connected to the interface, and an address counter inserted between the output of the display device and the input of the buffer storage, said address counter being connected to the output of the readout cycle sensor or readout line sensor and to the input of the interface.

This permits quantitative assessment of the quality of the material being inspected.

Advantageously, the interface should comprise a transmitter-receiver unit, an interrupt controller, and a controller of the direct access to the computer memory, the transmitter-receiver unit being inserted between the computer device and the buffer storage and connected to the display device.

This makes the flaw detector still more reliable in operation.

BRIEF DESCRIPTION OF THE DRAWINGS.

The invention will now be described in greater detail with reference to a specific embodiment thereof, in conjunction with the accompanying drawings, wherein.

DESCRIPTION OF THE PREFERRED EMBODIMENT

A method of magnetographic quality inspection of a material will now be described with reference to a specific embodiment thereof as applied to quality testing of welded joints.

Figure 1:
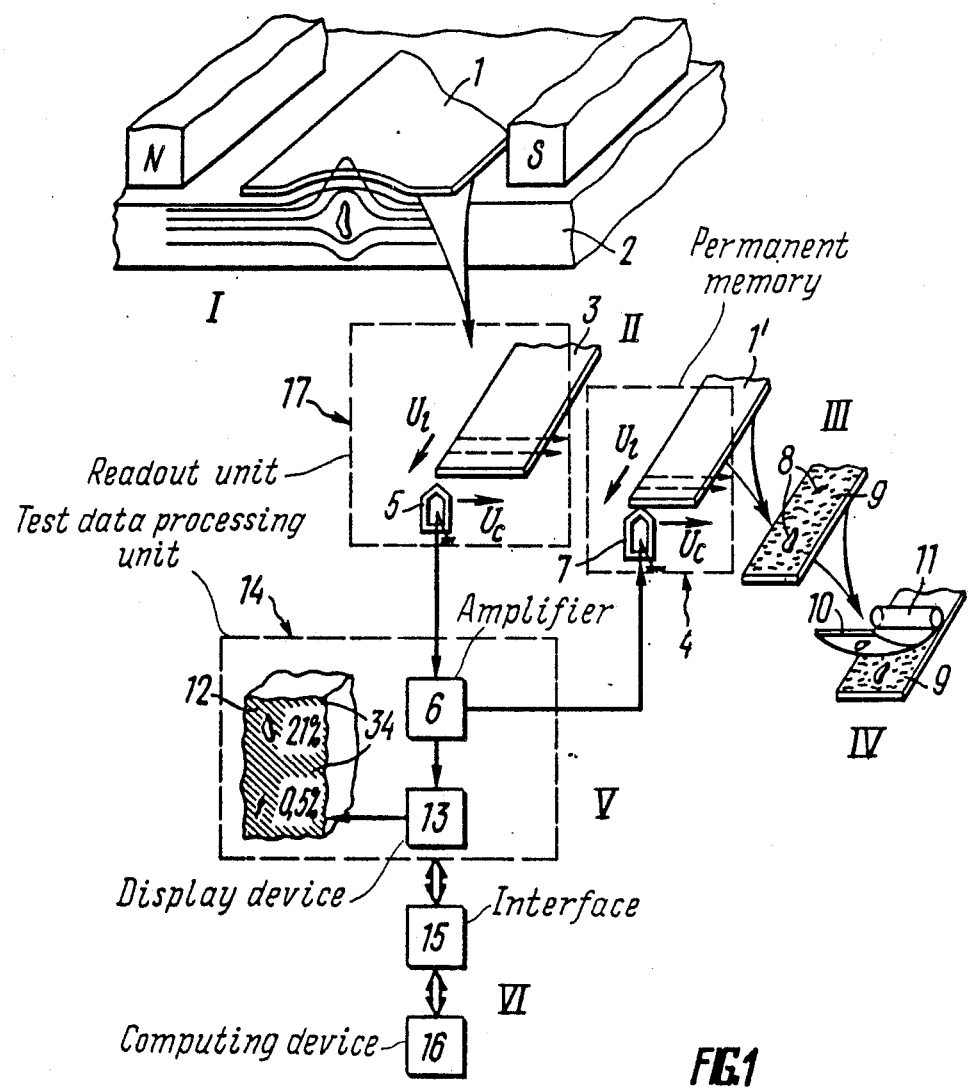
FIG. 1 shows schematically a method of magnetographic quality inspection of a material, according to the invention.

The method of magnetographic quality inspection of materials, according to the invention, comprises the following basic steps (FIG. 1).

Step I.

A magnetic medium 1 is applied onto a zone of a material 2 to be inspected, e.g. a welded joint. Then the tested material 2 and the magnetic medium 1 placed thereon are magnetized. FIG. 1 shows only parts of poles N-S of the electromagnet. In this manner, a magnetogram 3 is obtained, which characterizes the quality of the tested material 2.

Step II.

Information obtained in Step I is read, amplified, and recorded in the permanent memory.

To this end, the magnetogram 3 and the permanent memory 4, which in this embodiment is another magnetic medium 1' analogous to the magnetic medium 1, are transported simultaneously in relation to a magnetosensitive transducer 5 and a recording magnetic head 7 connected to said transducer 5 via an amplifier 6.

Step III.

Information recorded on the magnetic medium 1' of the permanent memory 4 is exposed.

To this end, a magnetosensitive powder or fluid is applied on the magnetic medium 1' on which the magnetogram 3 is recorded after amplification. Magnetic particles of the powder or fluid contain pigments or other elements sharply contrasting with the surface of the magnetic medium 1' of the permanent memory 4. These magnetic particles contained in the magnetosensitive substance are concentrated near magnetized zones caused by the flaws in the material 2 being inspected for quality. These particles form flaw patterns 8 and in this way repeat the pattern of the magnetic fields of such flaws in the material 2.

The pattern obtained on the basis of information recorded in the permanent memory 4 is referred to as a ferrogram 9.

Step IV.

The ferrogram obtained in Step III is duplicated and the required number of copies is made.

To this end, a common paper tape 10 is applied on the ferrogram 9 and rolled down by a roller 11 in order to achieve close contact of the ferrogram 9 and the paper tape 10. The pattern of the ferrogram 9 is copied on the paper tape 10 and can be used for documenting the test data. It should be noted that duplication of information from the ferrogram 9 to the paper tape 10 can be done by any other known methods of contact printing.

Step V.

Concurrently with the operations of Steps II and III, and independently therefrom, the output of the amplifier 6 is converted into indication signals which are indicated as either a color-and-shadow picture supplying qualitative characteristics of the material 2 or a digital characteristic supplying a quantitative assessment of the quality of the material 2.

The information is displayed on a screen 12 of a display device 13 of a test data processing unit 14.

Step VI.

The quantitative evaluation of the quality of the tested material 2 is performed by means of a computing device 16 connected to the test data processing unit 14 via an interface unit 15.

Information is read from the magnetogram 3 by the magnetosensitive transducer 5, converted into a digital form in the test data processing unit 14, and subjected to program-driven digital analysis in the computing device 16. Information obtained during one operational cycle of the magnetosensitive transducer 5, when this transducer 5 travels in relation to the magnetogram 3 to read one line, is summed up and the total is compared with other totals obtained during previous operational cycles of the transducer 5. The information signal is either the sum of signals during one cycle of operation of the transducer 5 or variation of this sum in different operational cycles of the transducer 5.

Referring to FIG. 2, the physics of the method of quantitative evaluation of the quality of the material 2 being tested is explained using a welded joint as an example.

FIG. 2 shows charts of the magnetic field $B_w$ (L) registered on the magnetic medium 1 (FIG. 1) in different areas of the tested material 2. Also shown are charts of the electrical signal f(t) produced by the magnetosensitive transducer 5 during line-after-line cyclic reading of the magnetic recording from the magnetogram 3. In FIG. 2d, $A_w$ is the amplitude of the signal, which is the function of the shape of the welded joint, and $A_{def}$ is the signal amplitude determined by the defect, when the magnetogram 3 is read by means of the transducer 5.

These charts demonstrate that variations of the amplitudes of the signals $B_{def}$(FIG. 2a) and $A_{def}$(FIG. 2d) are caused because the signal $B_w$ determined by the shape of the weld is difficult to tune off. Besides, comparison of the charts of FIGS. 2b and 2e demonstrates that the curve of the signal f(t) of the magnetosensitive transducer 5 contains no direct information on the size of the defect $B_{def}$(FIG. 2b).

Figure 2A:
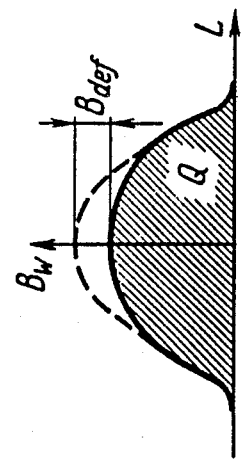
FIGS. 2a, b, d and e shows charts of the magnetic field, explanatory of the method of quantitative assessment of the quality of materials, according to the invention.
Figure 2B:
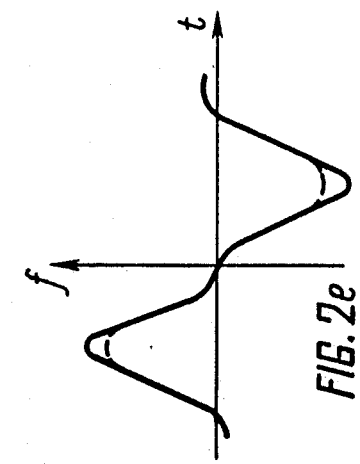
Figure 2D:
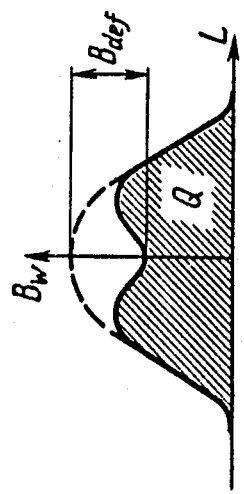
Figure 2E:
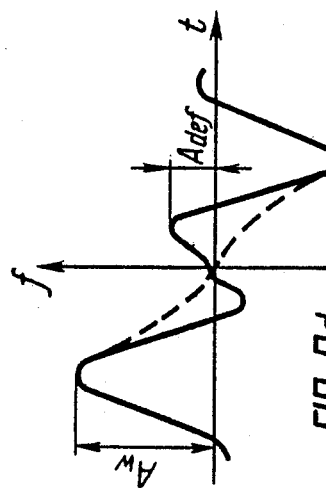

But charts of FIGS. 2a and 2b indicate that the quality of the material 2 being inspected can be unambiguously evaluated using the area Q under the curve $B_w$(L) indicating the magnitude of the variation of the magnetic field across the width of the magnetogram 3 during one operational cycle of the transducer 5. Reduction of this area is usually an indication of a defect. The dotted line curves of FIGS. 2a and 2b indicate a defect-free portion of the material 2 being inspected.

To summarize, quantitative evaluation of the quality of the tested material 2 can be made on the basis of the area under the curve indicating variation of the magnetic induction throughout the width of the magnetogram 3 during one operational cycle of the transducer 5. This area Q can be obtained by summing the signals read by the transducer 5 in one line from the magnetogram 3.

Besides, there is another parameter which can be used to make quantitative assessment of the quality of the tested material. This is the difference of the averaged values of the totals of several operational cycles of the transducer 5.

The proposed method of magnetographic quality inspection offers, therefore, a twofold advantage of reproducing a magnetogram by a high-sensitivity magnetic transducer and documenting this magnetogram by direct conversion into a ferrogram, which can be transferred to a common paper tape by contact methods.

Documenting of test data by means of a ferrogram and its copying is evidently a more advantageous method as contrasted to strip chart plotters and recorders because a ferrogram is much easier to obtain and then use to produce copies within a very short time. The ferrogram obtained by the proposed method has extremely good resolution because the original magnetogram, which is later transformed into the ferrogram, can be recorded on the magnetic medium of the permanent memory with almost any contrast degree.

Besides, as distinct from all prior art methods of magnetographic quality inspection of materials, the method according to the invention offers the advantage of making quantitative assessment of the cross-section of the material in the tested zone, which is made less by the defect, and not of the size of the defect itself. In consequence, the method provides quantitative assessment directly representing the quality of the material being tested.

To summarize, the method of magnetographic quality inspection of a material, according to the invention, is uncomplicated to carry out, produces extremely graphic test data, and can be used to inspect materials having complex shapes, e.g. welded joints, and particularly those located in places which are not easily accessible.

Figure 3:
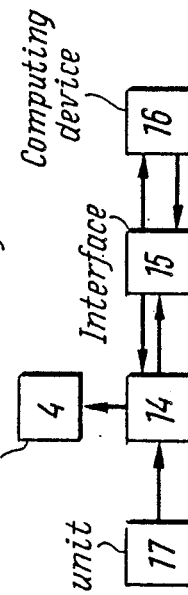
FIG. 3 shows a block diagram of a flaw detector realizing the method of magnetographic quality inspection of a material, according to the invention.

A flow detector realizing the method of magnetographic quality inspection of materials can have different embodiments. One embodiment (FIG. 3) of the flaw detector comprises several series-connected elements, namely a readout unit 17, a test data processing unit 14, an interface unit 15, and a computing device 16. It also comprises a permanent memory 4 which is connected to the test data processing unit 14.

Figure 4:
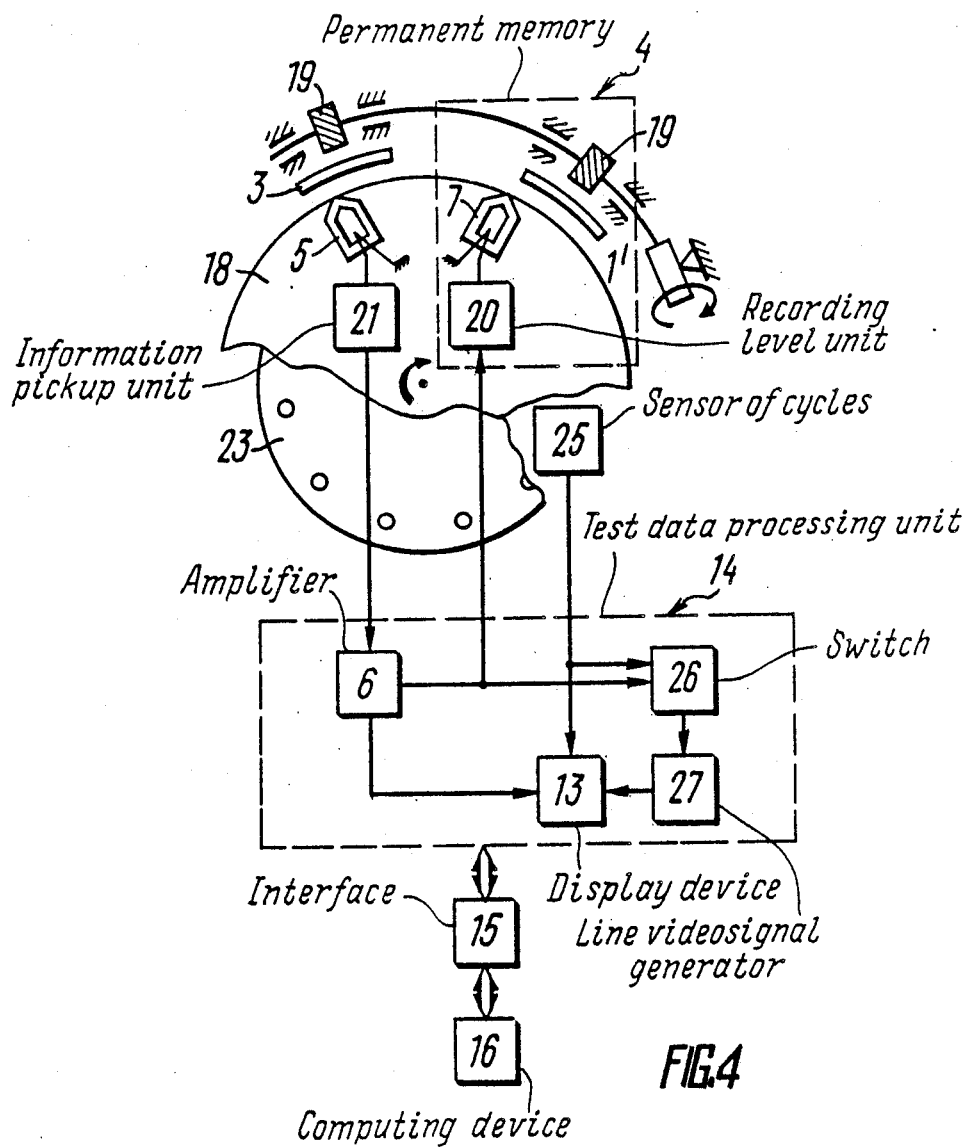
FIG. 4 shows a plan view of an embodiment of a readout unit of the flaw detector, which comprises a permanent memory and a recording magnetic head, according to the invention.

The readout unit 17 (FIG. 4) comprises a drum 18 adapted to rotate about the axis thereof, a mechanism for driving the magnetogram 3 together with magnetic medium 1 of the permanent memory 4 in relation to the drum 18. A magnetosensitive transducer 5 and a recording magnetic head 7 of the permanent memory 4 are arranged on the cylindrical surface of the drum 18. The recording magnetic head 7 is connected to a recording level unit 20 which can also be incorporated into the permanent memory 4. The readout unit 17 also comprises (FIG. 5) an information pickup unit 21, and a drum shaft 22, a modulation disk 23 provided with holes arranged along the perimeter thereof being secured on said drum shaft 22. The disk 23 is located between a light source 24 and a sensor 25 of cycles or lines. The light source 24 and the sensor 25 are placed on a straight line lying in the plane extending through one of the reproducing magnetic heads of the magnetosensitive transducer 5.

The test data processing unit 14 comprises two series connected elements: an amplifier 6 whose input is connected to the information pickup unit 21, and a display device 13.

The magnetosensitive transducer 5 of the readout unit 17 (FIG. 5) can be made up of several reproducing magnetic heads which are arranged on the cylindrical surface of the drum 18 with a displacement to the drum shaft 22 with a pitch "A" equal to the width of the readout line. These reproducing heads are spaced apart to a distance L equal to the length of the readout line, which is comparable to the width of the magnetogram 3 (FIG. 1). The test data processing unit 14 (FIG. 5) comprises a switch 26 whose inputs are connected respectively, to the sensor 25 of cycles or readout lines and the amplifier 6, while the output thereof is connected to the input of the display 13. The test data processing unit 14 can also comprise a line video signal generator 27 inserted between the output of the switch 26 and the input of the display 13. The display 13 has a screen 12 to monitor the results of testing.

Figure 6:
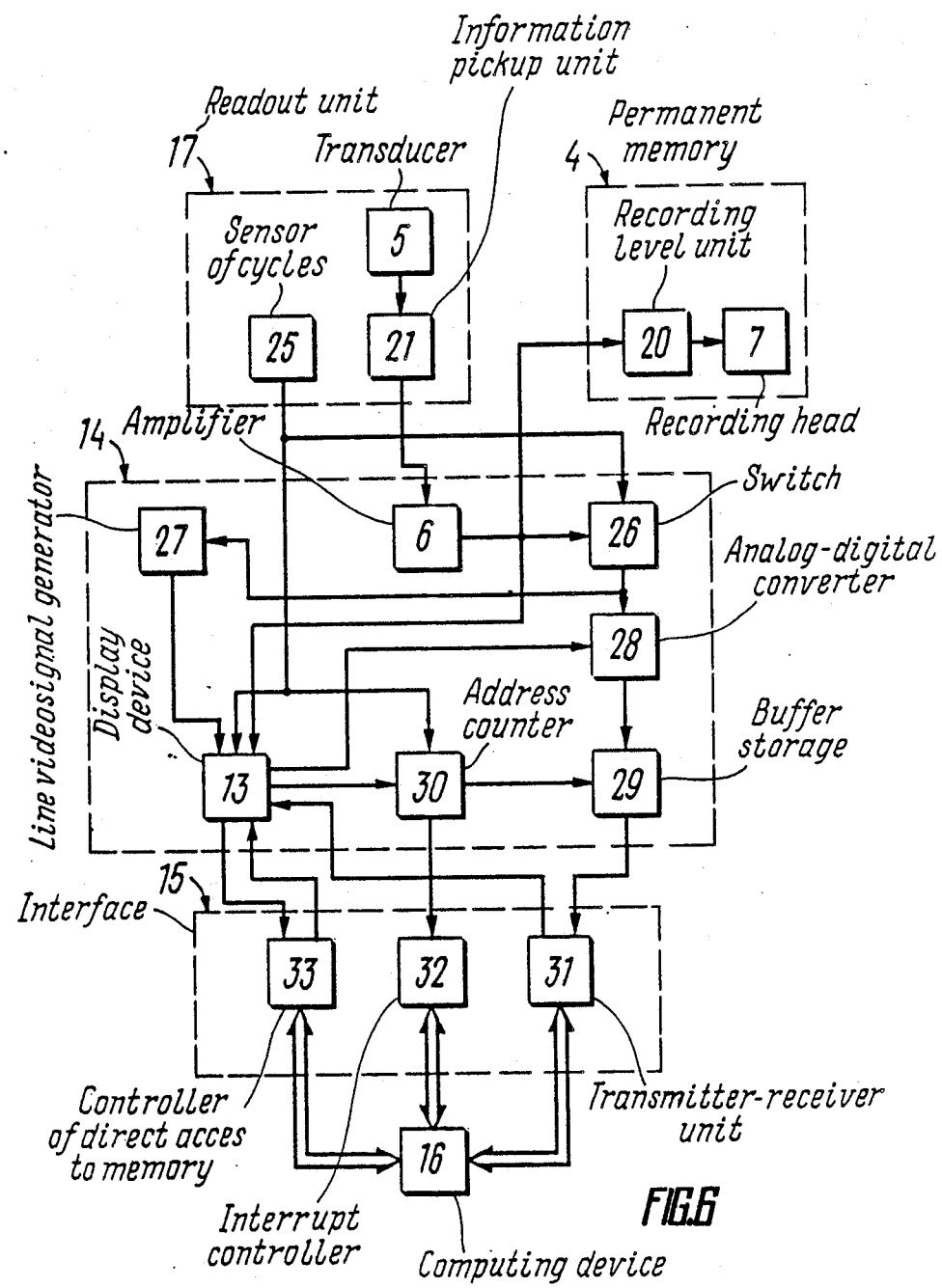
FIG. 6 shows a block diagram of an embodiment of a test data processing unit and its connections with interface and computing devices, according to the invention.

In order to realize the method of magnetographic quality inspection of materials in terms of quantitative assessment of the material quality, the test data processing unit 14 (FIG. 6) can comprise two series-connected elements: an analog-digital converter 28 whose inputs are connected to respective outputs of the switch 26 and the display 13, and a buffer storage 29 connected to the interface 15. It also comprises an address counter 30 whose inputs are connected to the sensor 25 of the readout unit 17 and the display device 13, while the outputs thereof are connected to the buffer storage 29 and interface 15.

The interface unit 15 (FIG. 6) can comprise a transmitter-receiver unit 31 inserted between the buffer storage 29 and the computing device 16. It also comprises an interrupt controller 32 connected to the display 13 and inserted between the address counter 30 and the computing device 16, and a controller 33 of the direct access to the memory of the computing device 16, which is inserted between the display device 13 and the computing device 16.

The foregoing proves that the block diagram of the flaw detector realizing the method of magnetographic quality inspection of materials consists of commonly used components which are well known to any person skilled in the art.

Thus, for example, the display device has been described in literature (cf., for example, Defektoskopiya, No. 7, 1985, pp. 42–48) and is used here for its direct purpose.

The flaw detector realizing the method of magnetographic quality inspection operates as follows.

The magnetosensitive transducer 5 (FIG. 4) and the recording magnetic head 7 installed in the drum 18 simultaneously scan the magnetogram 3 and the magnetic medium 1' of the permanent memory 4, respectively, which are transported in relation to the drum 18 by means of the mechanism 19. The mechanism 19 is installed on the motor shaft (not shown in FIG. 4). The information signal read by the transducer 5 is supplied to the amplifier 6 of the test data processing unit 14. After the amplifier 6, the information signal is fed to the recording level unit 20 connected to the recording head 7. Simultaneously, the information signal is fed from the output of the amplifier 6 to the display device 13. The recording head 7 records the magnetogram 3 (FIG. 1) with the desired contrast level into the permanent memory 4, e.g. the magnetic medium 1'. The high-constrast recording of the magnetogram 3 obtained on the magnetic medium 1' of the permanent memory 4 is then transformed, by any known method, into the ferrogram 9. The ferrogram 9 can be obtained by applying a magnetosensitive powder on the magnetic medium 1' of the permanent memory 4, as described in Step III of the method of magnetographic quality inspection.

The advantages of the method of documenting the magnetographic test data by means of a ferrogram, as compared to registering information signals by means of strip chert recorders, consist in that the information content of the test is increased and the flaw detector is made simpler.

Concurrently with the recording of information signals read from the magnetogram 3 (FIGS. 1 and 4), the flaw detector converts these signals into a color and shadow image by means of the display device 13 of the test data processing unit 14.

This is accomplished as follows.

Figure 5:
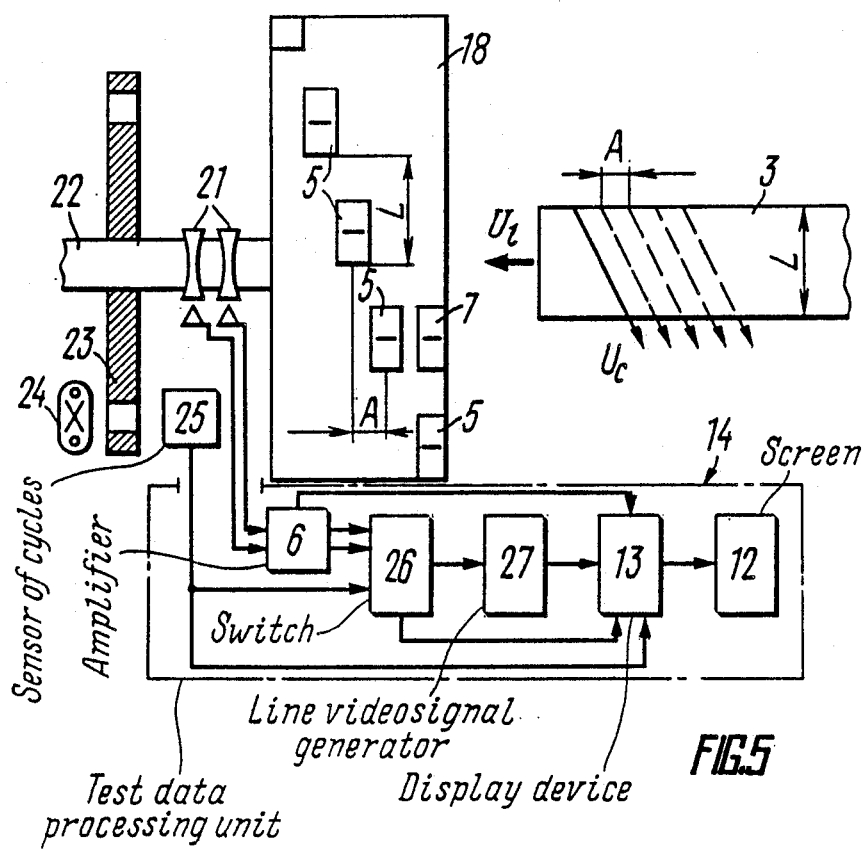
FIG. 5 shows a side view of an embodiment of a readout unit of the flaw detector, wherein the magnetosensitive transducer comprises several reproducing magnetic heads to obtain a color and shadow picture, according to the invention.

As the drum 18 (FIG. 5) rotates, the reproducing heads of the magnetosensitive transducer 5 run, with the pitch "A", over the magnetogram 3 and read, line after line, the recording, as shown by dotted lines in FIG. 5. In this case, one of the heads of the transducer 5 (FIG. 4), which is connected, via the amplifier 6 and the recording level unit 20, to the recording head 7, records the magnetogram 3 in the permanent memory 4. As each head of the transducer 5 (FIG. 5) runs over the magnetogram 3, the sensor 25 of lines or cycles generates a sweep trigger pulse for the display device 13, the speed of rotation of the drum 18 in this case dictates the frame frequency of the display device 13.

To summarize, the scanning of the transducer 5 over the magnetogram 3, as shown in FIG. 5, is synchronized by the sensor 25 with the electronic beam travelling on the screen 12 of the display device 13. The magnetogram 3 is, therefore, reproduced in a line-after-line manner. In this case, the switch 26 of the test data processing unit 14 connects the input of the line videosignal generating unit 27, in synchronism with the rotation frequency of the drum 18, to the reproducing heads of the transducer 5. The information signal fed from the magnetosensitive transducer 5 is mixed, in the line videosignal generating unit 27, with the sync signals fed from the sensor 25. Thus, for example, when the drum 18 rotates with a speed of 50 rps and its diameter is 170 mm, the number of reproduced lines $Z=32$. This corresponds to a television frame with a width $L=33$ mm and the test zone length $X=64$ mm.

The resolution of this system for obtaining a color and shadow picture is dictated by the number of picture elements within a frame $$N_k = \frac{x}{2} Z^2 \approx 2{,}000.$$

This corresponds to reproduction of information from the area of 1 mm$^2$, which is at least by one order of magnitude greater than the area of the magnetic image caused by an internal defect. Considering that the magnetosensitive transducer 5 responds to the sign of magnetization, the resolution can be even higher. The flaw detector featuring the simplest embodiment of the transducer 5 equipped with 32 reproducing heads possesses, therefore, adequate resolution.

A serious advantage of this display system consists in that a moving magnetogram 3 (FIG. 5) can be examined. Even if the magnetogram 3 covers the length of the frame within 1 second, in other words the speed of the magnetic medium $V_l = 64$ mm/sec, the speed of magnetogram 3 is still much less than the frame repetition frequency of the picture being produced on the screen. In other words, the speed of the magnetic transducer $V_c$ is much greater than the speed of the magnetic medium $V_l$.

The flaw detector can also be used to obtain quantitative assessment of the quality of the material being inspected. This can be done as follows.

Signals of the magnetosensitive transducer 5 (FIG. 6) are fed, after the amplifier 6 and switch 26, to the analog-digital converter 28 whose output is a digital code. One cycle of the transducer 5 corresponds to n readings of the information signal. Discrete quantities of the information signal are supplied from the analog-digital converter 28 to the buffer storage 29, where they are recorded into storage cells whose addresses are dictated by the address counter 30 connected to the address input of the buffer storage 29. The address counter 30 counts sync pulses fed from the display device 13, when output pulses of the sensor 25 are applied to the gating input thereof. The overflow pulse is supplied from the output of the address counter 30 to the input of the interrupt controller 32 which produces a signal to switch the computing device 16 to service the subprogram for readout of information from the buffer storage via the transmitter-receiver 31 to the computing device 16. This subprogram also sums up the readings obtained during one cycle of the transducer 5. The total is supplied, via the direct access controlled 33, to the display 13 and is shown on the screen 12 (FIG. 1) as the digital reading 34.

The method of magnetographic quality inspection of materials and the flaw detector realizing this method offer the advantages of detecting internal defects in workpieces of complex shapes and determining the size of these defects, including defects of welded joints having reinforcement beads, when access is only possible from one side. No cleaning of the workpiece surface is required.

The sensitivity and resolution of the method and device are high enough to permit automatic quality testing. A paper document substantiating the test results can be obtained by an uncomplicated and reliable technique.

In addition, the flaw detector, according to the invention, permits scaling and visualization of the internal state of the tested material, using a "traffic light" principle, when inadmissibly large defects are indicated by red color on the screen. Besides, the flaw detector is easy to operate and highly reliable.

What is claimed is:

1. A flaw detector for magnetographic quality inspection, comprising:
    a readout unit having:
        a drum with a cylindrical surface adapted to rotate about a shaft thereof;
        a magnetosensitive transducer disposed on the cylindrical surface of said drum;
        a modulation disk featuring holes arranged along the perimeter thereof and installed on the shaft of said drum;
        a sensor of lines, installed in the immediate vicinity of said holes of said modulation disk;
        a mechanism for driving a magnetogram and said drum with said magnetosensitive transducer;
        a test data processing unit having:
            an amplifier whose input is connected to said magnetosensitive transducer;
            a display device having at least five inputs and three outputs, the first said input being connected to an output of said amplifier, the second said input being connected to said line sensor;
        a permanent memory comprising:
            a magnetic medium disposed in said mechanism for driving said magnetogram and magnetosensitive transducer;
            at least one recording magnetic head electrically coupled to said amplifier.

2. A flaw detector as claimed in claim 1, wherein said magnetosensitive transducer is made as at least one reproducing magnetic head, said recording head of said permanent memory being disposed on the cylindrical surface of said drum so that it is displaced circumferentially in relation to said reproducing magnetic head, while said mechanism for driving the magnetogram and magnetosensitive transducer is additionally provided with a device for carrying said magnetic medium of said permanent memory.

3. A flaw detector as claimed in claim 1, wherein said magnetosensitive transducer comprises several reproducing magnetic heads arranged on said cylindrical surface of the drum so that they are displaced along the shaft of said drum and each next reproducing magnetic head is spaced from the previous one at a distance equal to the length of a sensed line, said test data processing unit additionally comprising a switch having inputs whose number is greater than the number of said reproducing magnetic heads and which are connected to said amplifier and said line sensor, while the output thereof is connected to said second input of said display device.

4. A flaw detector for magnetographic quality inspection, comprising:
    a readout unit having a drum with a cylindrical surface, which is adapted to rotate about a shaft thereof;
    a magnetosensitive transducer disposed on the cylindrical surface of said drum and comprising several reproducing magnetic heads arranged on said cylindrical surface of the drum so that they are displaced along the shaft thereof, each next reproducing magnetic head being spaced from the previous one at a distance equal to the length of a sensed line;
    a modulation disk having holes along the perimeter thereof and installed on the shaft of said drum;
    a sensor of cycles, installed in the immediate vicinity of said holes of said modulation disk;
    a mechanism for driving a magnetogram and said drum with the magnetosensitive transducer;
    a test data processing unit having: an amplifier whose input is connected to said magnetosensitive transducer;
    a display device having at least five inputs and three outputs, said first input being connected to an output of said amplifier, said input being connected to said sensor of cycles;
    a switch having one input connected to said sensor of cycles and another input connected to said amplifier, and having an output;
    a line videosignal generator having an input connected to said output of said switch, while the output thereof is connected to said third input of said display device;
    at least one recording magnetic head electrically connected to said amplifier;
    an interface connected to an output of said test data processing unit, and
    a computing device having at least three inputs and three outputs and connected to an output of said interface.

5. A flaw detector as claimed in claim 4, wherein said test data processing unit additionally comprises:
    an analog-digital converter having two inputs and an output; said first input being connected to said switch, said second input being connected to said first output of said display device;
    a buffer storage whose input is connected to said output of said analog-digital converter, while the output thereof is connected to said interface;
    an address counter having at least two inputs and two outputs, whose respective inputs are connected to said sensor of cycles or sensed lines and to said second output of said display device, while respective outputs are connected to said buffer storage and said interface.

6. A flaw detector as claimed in claim 5, wherein said interface comprises:
    a transmitter-receiver unit having at least two inputs and two outputs; said first input connected to said buffer storage, said second input connected to said computing device, said first output connected to said fourth input of said display device, said second output connected to said computing device;

interrupt controller having at least two inputs and an output; said first input connected to said address counter, said second input and said output connected to said computing device;

controller of the direct access to a memory, having at least two inputs and two outputs; said first input connected to said third output of said display device, said second input connected to said computing device, said first output connected to said fifth input of said display device, and said second output connected to said computing device.

7. A flaw detector for magnetographic quality inspection, comprising:

a readout unit having:

a drum with a cylindrical surface, which is adapted to rotate about the shaft thereof;

several reproducing magnetic heads arranged on the surface of said drum so that they are displaced along the shaft thereof, each next reproducing magnetic head being spaced from the previous one at a distance equal to the length of a sensed line;

a modulation disk having holes along the perimeter thereof, which is installed on the shaft of said drum;

sensor of cycles or lines, installed in the immediate vicinity of said holes in said modulation disk;

a mechanism for driving a magnetogram and said drum with said reproducing magnetic heads;

a test data processing unit having:

an amplifier having several inputs and outputs whose number is equal to the number of reproducing heads to which they are connected;

a switch connected to said outputs of said amplifier and to an output of said sensor of cycles or lines; a display device having at least five inputs and three outputs; said firs input connected to the output of said amplifier, said second input connected to said sensor of cycles and lines;

a line video signal generator whose input is connected to said switch, while the output thereof is connected to said third input of said display device;

an analog-digital converter having at least two inputs and an output, said first input connected to said switch, said second input connected to said first output of said display device;

a buffer storage having at least two inputs and an output, one input connected to said output of the analog-digital converter;

an address counter having at least two inputs and two outputs, said first input connected to said sensor of cycles or lines, said second input connected to said second output of said display device, said first output connected to the other said input of the buffer storage;

an interface connected to the output of said test data processing unit, and comprising: a transmitter-receiver unit having at least two inputs and two outputs, said first input connected to said output of the buffer storage, said first output connected to said fourth input of said display device; an interrupt controller having at least two inputs and an output, one said input connected to said second output of the address counter;

a controller of the direct access to a memory, having at least two inputs and two outputs; said first input connected to said third output of said display device;

a computing device having at least three inputs and three outputs; said first input connected to said second output of said transmitter-receiver unit, said second input connected to said interrupt controller, said third input connected to said second output of said controller of the direct access to a memory of said computing device, said first output connected to said second input of the transmitter-receiver unit, said second output connected to said second input of the interrupt controller, and said third output connected to said second input of the direct access controller.

* * * * *